(12) United States Patent
Scala

(10) Patent No.: US 8,475,358 B2
(45) Date of Patent: Jul. 2, 2013

(54) SEXUAL ENHANCEMENT LUBRICATION POWDER

(76) Inventor: Jessica Scala, Latham, NY (US)

( * ) Notice: Subject to any disclaimer, the term of this patent is extended or adjusted under 35 U.S.C. 154(b) by 1014 days.

(21) Appl. No.: 12/505,805

(22) Filed: Jul. 20, 2009

(65) Prior Publication Data

US 2011/0015481 A1    Jan. 20, 2011

(51) Int. Cl.
*A61F 5/00*    (2006.01)

(52) U.S. Cl.
USPC .......................................................... 600/38

(58) Field of Classification Search
USPC ................................ 600/38–41; 424/439–442
See application file for complete search history.

(56) References Cited

U.S. PATENT DOCUMENTS

| | | | |
|---|---|---|---|
| 3,955,009 A | 5/1976 | Eskritt et al. | |
| 4,157,386 A | 6/1979 | La Rochelle | |
| 4,168,323 A | 9/1979 | Inamine et al. | |
| 4,997,654 A | 3/1991 | Corsello et al. | |
| 5,098,730 A | 3/1992 | Pepper et al. | |
| 6,054,119 A | 4/2000 | Hurme et al. | |
| 6,241,997 B1 | 6/2001 | Kershman et al. | |
| 6,375,982 B1 | 4/2002 | Cherukuri | |
| 6,406,717 B2 | 6/2002 | Cherukuri | |
| 6,589,556 B2 | 7/2003 | Cherukuri | |
| 2002/0071871 A1 | 6/2002 | Snyder et al. | |
| 2007/0031561 A1 | 2/2007 | Lakkis et al. | |
| 2007/0292371 A1 | 12/2007 | Clarot et al. | |
| 2008/0241080 A1 | 10/2008 | Rodriguez-Vilaboa | |
| 2009/0035227 A1 | 2/2009 | Hausmanns et al. | |
| 2009/0053309 A1 | 2/2009 | Domb et al. | |
| 2009/0081294 A1 | 3/2009 | Gin et al. | |

FOREIGN PATENT DOCUMENTS

| | | |
|---|---|---|
| JP | 2001288076 | 10/2001 |
| WO | 2009047236 A1 | 4/2009 |

*Primary Examiner* — John Lacyk
(74) *Attorney, Agent, or Firm* — Schmeiser, Olsen & Watts LLP

(57) ABSTRACT

Provided is a dry, edible, sexual enhancement lubricant powder. The powder comprises a powdered sweetening agent which is also a sialogogue; a powdered thickening agent, which is combined with the sweetening agent/sialogogue; and a powdered flavoring agent, which is combined with the sweetening agent/sialogogue and thickening agent. Human saliva, when added to the dry powdered composition, effectuates the transformation of the composition into a gel-like lubricant useable for sexual enhancement. Also provided is a method of sexual enhancement using the sexual enhancement lubrication powder.

19 Claims, No Drawings

SEXUAL ENHANCEMENT LUBRICATION POWDER

FIELD OF THE INVENTION

This invention relates generally to sexual enhancement aids, and specifically to a flavored powder that stimulates the production of saliva when introduced to a mouth, and when mixed with saliva becomes a gel-like sexual lubricant.

BACKGROUND OF THE INVENTION

It is common for individuals engaged in sexual activity to employ various sexual aids to enhance pleasure. External-use flavored edible body powders are used to enhance sexual experiences by making oral contact with various body parts more enjoyable, particularly during oral-genital contact. Also, lubricants are commonly used to facilitate various sexual activities. Gel-like water-based lubricants are commonly employed sexual lubricants, and oil-based lubricants are also used. A lubricant is often useful to reduce friction between body parts used during sexual activity resulting in a more pleasurable experience. These gel lubricants are often flavored or scented but may be unpleasant to put into one's mouth. Saliva can act as a natural sexual lubricant if provided in sufficient quantity. However, often individuals engaged in sexual activity are unable to generate enough saliva to facilitate suitable lubrication, or the saliva generated is of insufficient viscosity to render effective lubrication. Hence, a need exists to provide a sexual aid that promotes elevated saliva production to facilitate the transformation of a flavored powder into a sexually enhancing gel-like lubricant.

SUMMARY OF THE INVENTION

The present invention provides a composition for an edible sexual enhancement lubrication powder.

A first aspect of the present invention provides a dry, edible, sexual enhancement lubricant powder composition comprising: a dry, powdered sweetening agent which is also a sialogogue, a dry, powdered thickening agent, which is combined with the sweetening agent/sialogogue; a dry, powdered flavoring agent, which is combined with the sweetening agent/sialogogue and thickening agent; the composition such that whereupon the addition of human saliva to the dry, powdered, edible composition, effectuates the transformation of the composition into a gel-like lubricant useable for sexual enhancement.

A second aspect of the present invention provides A dry, edible, sexual enhancement lubricant powder composition comprising: dry, powdered xylitol, used as a sweetener/sialogogue; a dry, powdered gelatinizing viscosity enhancer which provides for an increase in viscosity of a composition without substantially modifying its other properties, improving suspension of ingredients of a composition, the gelatinizing viscosity enhancer being combined with the xylitol; a dry, powdered flavoring agent, which is combined with the xylitol and gelatinizing viscosity enhancer wherein the flavoring further comprises: a dextrose base powder, and at least one natural flavor; the composition such that whereupon the addition of human saliva to the dry, powdered, edible composition, effectuates the transformation of the composition into a viscous semi-rigid colloid useable as a personal lubricant.

A third aspect of the present invention provides a method of sexual enhancement comprising: providing a dry, edible, sexual enhancement lubricant powder composition comprising: a dry, powdered sweetening agent which is also a sialogogue, a dry, powdered thickening agent, which is combined with the sweetening agent/sialogogue; a dry, powdered flavoring, which is combined with the sweetening agent/sialogogue and the thickening agent, wherein the flavoring further comprises: a dextrose base powder, and natural flavors; the composition such that whereupon the addition of human saliva to the dry, powdered, edible composition, the composition transforms into a gel-like lubricant useable for sexual enhancement; applying the dry, edible sexual lubricant powder to an external human body part; adding human saliva to the dry, edible sexual enhancement lubricant powder; and using the mixture of dry, edible sexual lubricant powder and human saliva as a sexual lubricant.

The foregoing and other features of the invention will be apparent from the following more particular description of various embodiments of the invention.

DETAILED DESCRIPTION

Although certain embodiments of the present invention are shown and described in detail, it should be understood that various changes and modifications may be made without departing from the scope of the appended claims. The scope of the present invention will in no way be limited to the number of constituting components, the materials thereof, the quantities thereof, the relative arrangement thereof, etc., and are disclosed simply as an example of embodiments of the present invention.

As a preface to the detailed description, it should be noted that, as used in this specification and the appended claims, the singular forms "a", "an" and "the" include plural referents, unless the context clearly dictates otherwise.

Embodiments of a sexual enhancement lubrication powder, as described herein, may be a flavored edible body powder, of the kind that is put on the external surface of various body parts and for sexual enhancement can be desirably mixed with a liquid, such as saliva, to become a viscous, gel-like lubricant, usable for facilitating and enhancing a sexual experience. Embodiments of a sexual enhancement lubrication powder, as described herein, may allow one or more people to enhance their sexual experience by having an external-use, dry, flavored body powder, which, may be applied to a body part(s) and, upon contact of the powder-covered body part with the mouth, stimulates production of saliva, a natural lubricant, while at the same time transforming the powder into an appropriately viscous gel-like sexual lubricant.

In one embodiment, the edible sexual enhancement lubrication powder comprises a sweetener that is also a sialogogue, a thickening agent, and a flavoring agent. Whereas embodiments of the sexual enhancement lubrication powder, as described herein, may be a dry powder, the ingredients comprising the powder may be in a dry, powdered form, where powder denotes a substance that may comprise a desiccated, anhydrous substance such as one generally formed by crushing or pulverizing a solid, consisting of fine loose grains which are easily measured, sifted, mixed and do not undergo any significant reaction, chemical, thermal, or otherwise, when combined. An embodiment of the edible sexual enhancement lubrication powder may be of a consistency similar to powdered sugar. In other embodiments other powdered ingredients, such as aroma enhancers, color enhancers, preservatives, desiccants, organic glitter, glow-in-the-dark elements, etc., may be added.

As pertaining to other embodiments of an edible sexual enhancement lubrication powder, the dry powder composition comprising a sweetener which is also a sialogogue, a thickening agent, and a flavoring agent, when mixed with a liquid substance, such as human saliva, transforms from a dry powder to a gel-like viscous lubricant suitable for use as a sexual enhancement lubricant. Embodiments of a sexual enhancement lubrication powder, as described herein, upon the addition of human saliva, transform into a gel-like substance which may have the properties of a semi-rigid, jelly-like solid, being a colloidal suspension of a solid dispersed in a liquid in which the disperse phase (dry powder) has combined with the dispersion medium (human saliva) and exhibits little or significantly reduced flow in a steady state condition. Embodiments of the sexual enhancement lubricant, after saliva is added as described herein, are satisfactory for sexual enhancement when the viscous gel-like lubricant has sufficient internal resistance to flow to allow the lubricant to remain on the portion of the body on which it has been placed, without readily flowing off due to gravitational effects, and to provide a suitable friction-reducing layer to mitigate potentially adverse effects of direct contact between two surfaces (such as two body parts) by reducing the heat and/or skin abrasion produced by friction which could otherwise cause pain or discomfort resulting from loss of the outer skin layer, blistering, burning, cuts, rawness, lacerations, etc.

In another embodiment of the invention, the composition may comprise a sweetener/sialogogue such as xylitol, isomalt, mannitol, maltitol, sorbital, aspartame, acesulfame K, aspartamel, or other polyol with similar capacity to impart a sweet taste when the sexual enhancement lubricant powder contacts a person's tongue, and the capacity to stimulate enhanced production and saliva flow from salivary glands when the sweetener/sialogogue is taken into a person's mouth. The sweetener/sialogogue may also comprise a combination of a food grade acid such as, ascorbic acid or citric acid, and a sweetener taken from the above list.

In another embodiment of the invention, the thickening agent may be any dry, powdered gelatinizing viscosity enhancer that increases the internal resistance to flow of a solid phase when a liquid phase is added without substantially modifying other properties, improves suspension of solid ingredients of a composition in a liquid phase, and transforms a dry, powdered composition, upon the addition of liquid (human saliva), into a gel-like water based lubricant having similar properties to water-based liquid personal lubricants well known in the art. The thickening agent may be, but is not limited to, lecithin derived from soy or egg sources, corn starch, potato starch, fecula, arrow root, katakuri starch, sago, tapioca, collagen, furcellerum, carageenan, algar, alginate, guar gum, locust bean gum, xanthan gum, a mixed ester of glycerol and choline, mono- and di-glycerides of fatty acids and their esters, phosphated monoglycerides, or other food grade phospholipids.

The powdered flavoring agent may be one of many flavoring powders comprising a base ingredient, such as dextrose or other powdered food grade filler or volume enhancer which does not impart a noticeable flavor and has a sweetness less than that of ordinary sugar (sucrose), and one or more natural or artificial flavors. A natural flavor may be an essential oil, oleoresin, essence or extractive, mineral, protein hydrolysate, distillate, or any product of roasting, heating or enzymolysis, which contains the flavoring constituents derived from a spice, fruit or fruit juice, vegetable or vegetable juice, edible yeast, herb, bark, bud, root, leaf or similar plant material, meat, seafood, poultry, eggs, dairy products, or fermentation products therefrom such that the natural flavor, as combined with the base ingredient, comprises a dry powder. The powdered flavoring agent may be a flavor powder such as those produced by Nature's Flavors™, Blue Pacific™, Gold Coast Ingredients Flavor Fusion®, Wild Flavors, Inc., Berry Farm Foods, and others.

The natural flavors may include, but are not limited to, the following flavors: Almond, Amaretto, Anise, Apple, Apricot, Banana, Banana Cream, Bavarian Cream, Blackberry, Black Cherry, Blueberry, Boysenberry, Brandy, Bubblegum, Butter, Butterscotch, Caramel, Caramel Apple, Champagne, Cheesecake, Cherry, Cherry Vanilla, Chocolate, Chocolate Mint, Cinnamon, Citrus Punch, Clove, Coconut, Cola, Cookies and Cream, Cotton Candy, Cranberry, Dragonfruit, English Toffee, Fig, French Vanilla, Fruit Punch, Ginger, Gingerbread, Grape, Grapefruit, Guava, Hazelnut, Honey, Honeysuckle, Irish Cream, Juicy Fruit, Key Lime, Kiwi, Kiwi Lime, Kona, Lavender, Lemon, Lemondrop, Lime, Macadamia, Mandarin Orange, Mango, Maple, Melon, Mint, Mocha, Nutmeg, Orange, Papaya, Passionfruit, Peach, Peanut Butter, Pear, Pecan, Peppermint, Pina Colada, Pineapple, Pistachio, Plum, Praline, Pomegranate, Raspberry, Raspberry Truffle, Root Beer, Rum, Salsa, Sour Apple, Spearmint, Spice, Strawberry, Strawberry Cheesecake, Strawberry Kiwi, Tabasco, Tangerine, Tequila, Tropical Fruit, Vanilla, Watermelon, Wintergreen, or any combination of the foregoing or other natural flavors.

Because natural flavoring is often accomplished by using molecules that exhibit some degree of volatility and can be detected by the olfactory system, the flavoring agent may also act as an aroma enhancing agent. For example, although a natural cinnamon flavor may be added to enhance taste, it is apparent to those skilled in the art that the addition of cinnamon flavoring agent will produce a desirable aroma, thereby enhancing the aroma of the sexual enhancement lubrication powder. It should be obvious to one skilled in the art that cinnamon flavoring agent is used here as an example of the aroma enhancing properties of a flavoring agent, and the use of a flavoring agent as an aroma enhancing agent is not limited to cinnamon flavoring agent.

A sexual enhancement lubrication powder, as described herein, may comprise about 43%-73% sweetener/sialogogue (saliva promoting agent) by weight, about 0.3%-3% thickening agent by weight, and about 26%-55% flavoring agent by weight. More specifically, an embodiment of the composition may comprise about 54%-66% xylitol by weight, about 0.9%-1.1% lecithin by weight, and about 32%-45% natural flavoring agent by weight.

Embodiments of a sexual enhancement lubrication powder, as described herein, may be provided as part of a method of sexual enhancement. Accordingly, such sexual enhancement methodology may include the application of the flavored sexual enhancement lubricating powder to an external body part(s) of one or more persons, in particular genitalia or other erogenous zones. Further, the flavored powder may then be licked, taken into one's mouth, otherwise orally engaged, spit upon, or otherwise combined with human saliva. As the sexual enhancement lubricant powder contacts the mouth, the saliva-promoting agent (sialogogue) causes an increase in salivation. The stimulated saliva may mix with saliva already in the mouth, increasing the volume of saliva in the mouth and making more saliva available to mix with the sexual enhancement lubricant powder. The ingredients in the powder may combine with the saliva from the mouth and because of the thickening agent, the powder can transform into a gel-like, viscous substance which has sufficient internal resistance to flow that the gel can be applied to a body part and generally remain in its desired location, and is sufficiently thick to reduce friction between two surfaces that may be in rubbing contact. The resulting substance may be usable as a lubricant, such as those used in sexual applications. Because the experience of introducing a flavored powder on a body part into the mouth may be gustatorily pleasurable, use of this aspect of the invention heightens the sexual experience. Furthermore, the resulting lubricant can be used to further the sexual experience, without need to resort to another lubricating product. This double action (flavoring and lubricating) of embodiments of a sexual enhancement lubrication powder, as described herein, may lead to further enhancement and pleasure in a sexual experience.

To prepare an embodiment of a sexual enhancement lubricant powder, the component ingredients, particularly the sweetener/sialogogue preferably should be provided in a finely-powdered state. This may require the grinding of crystallized or granular ingredients into a fine powder. The finely ground powders may then be mixed, stirred, or otherwise combined. The composition may then be sifted at least once to add air to and increase the volume of the powder, resulting in a mixture that is lighter, fluffier, and less dense than the powder pre-sifting. Other optional powdered, dry ingredients may be added, such as a color enhancing agents, glow-in-the-dark agents, organic glitter, or preserving agents. Once the composition is prepared it may be put into packaging.

Embodiments of a sexual enhancement lubricant powder may optionally comprise a color enhancing agent such as a powdered food dye, a dispersion coloring agent such as a powdered aluminum or other metallic lake, natural colorings derived from natural sources such as but not limited to, annatto extract, beta-carotene, grape skin extract, cochineal extract or carmine, paprika oleoresin, caramel color, fruit and vegetable juices, saffron, etc., and the like, including any combination of the foregoing. Coloring agents may also comprise food substances that are colored powders such as powdered beverage mixes, baking coloring agents, and the like, or any combination of the foregoing. Embodiments of a sexual enhancement lubricant powder may optionally comprise a powdered, food-grade glow-in-the-dark agent exhibiting either phosphorescence, fluorescence, ultraviolet reactivity and the like which may increase pleasure in a sexual experience by adding a visually observable stimulus where the sexual enhancement lubricant powder either glows phosphorescently or under the influence of a source of ultraviolet light, such as a black light. Embodiments of a sexual enhancement lubricant powder may optionally comprise a preserving agent such as but not limited to a preservative such as sodium benzoate, calcium propionate, sodium erythorbate, sodium nitrite, calcium sorbate, sodium sorbate, potassium sorbate, BHA, BHT, EDTA, erythorbic acid, sodium diacetate, sodium succinate, grape seed extract, pine bark extract, apple extract, tea propylphenols, succinic acid, paraben, sodium dehydroacetate or tocopherols or any combination of the foregoing; or a dessicant or anti-caking agent, such as calcium silicate, iron ammonium citrate, silicon dioxide, magnesium carbonate, talc, bentonite, sodium aluminosilicate, kaolin, potato starch, or microcrystalline cellulose, or any combination of the above. It will be understood by one skilled in the art that the coloring agents, glow-in-the-dark agents, organic glitter, and preserving agents listed herein do not constitute an exhaustive list of possible additives, but are merely exemplary of substances that may be used to impart to the sexual enhancement lubricant powder the desired characteristics and attributes.

The following Examples are illustrative of various embodiments of the edible sexual enhancement body lubrication powder, as described herein, however, the scope of the invention is not intended to be limited by the specific details of the examples.

EXAMPLES

Example #1

|  | % by weight | amount in grams |
|---|---|---|
| Xylitol | 65.93 | 12 |
| Lecithin | 1.1 | 0.2 |
| Chocolate flavor powder (from Nature's flavors ™) | 32.97 | 7 |
|  | 100.00 | 19.2 |

In Example #1, granulated xylitol was crushed into a fine powder using a mortar and pestle. The Lecithin and chocolate flavor powder were added, and the mixture was sifted to add airiness to the mixture. In this combination the sweetness and flavor of the sexual enhancement lubrication powder was desirable, and when human saliva was added, a sexual lubricant of a desirable viscosity was obtained.

Example #2

|  | % by weight | amount in grams |
|---|---|---|
| Xylitol | 54.05 | 12 |
| Lecithin | 0.9 | 0.2 |
| Pear flavor powder (from Nature's flavors ™) | 45.05 | 10 |
|  | 100.00 | 22.2 |

In Example #2, granulated xylitol was crushed into a fine powder using a mortar and pestle. Lecithin and pear flavor powder were added, and the mixture was sifted to add airiness to the mixture. In this combination the sweetness and flavor of the sexual enhancement lubrication powder was desirable, and when human saliva was added, a sexual lubricant of a desirable viscosity was obtained. This example serves to illustrate the range of flavor powder that may be added to achieve a desirable flavor when using more subtle flavors, such as pear. Using more or less flavoring agent does not have a significant effect on sweetness and lubricant viscosity; changing the amount of flavor powder only significantly affects flavor. As the amount of flavoring agent is varied, the potency of the taste strengthens or diminishes depending on the amount of flavoring agent used; varying the amount does not affect the properties of the composition with regard to the lubricant resulting following saliva addition, and because the base of the flavoring agent may be dextrose is not as sweet as xylitol, more or less flavoring agent has only a minimal effect on the composition's sweetness.

Example #3

|  | % by weight | amount in grams |
| --- | --- | --- |
| Xylitol | 68.97 | 16 |
| Lecithin | 0.86 | 0.2 |
| Flavor powder (from Nature's flavors ™) | 30.17 | 7 |
|  | 100.00 | 23.2 |

In Example #3, granulated xylitol was crushed into a fine powder using a mortar and pestle. Lecithin and chocolate flavor powder were added, and the mixture was sifted to add airiness to the mixture. In this combination the flavor of the sexual enhancement lubrication powder was desirable, and when human saliva was added, a sexual lubricant of a desirable viscosity was obtained. However, with xylitol added near the upper acceptable limit, the powder became overly sweet. This example serves to illustrate the range of sweetener (xylitol) that may be added to achieve desirable sweetness.

Example #4

|  | % by weight | amount in grams |
| --- | --- | --- |
| Xylitol | 49.38 | 8 |
| Lecithin | 1.24 | 0.2 |
| Flavor powder (from Nature's flavors ™) | 49.38 | 8 |
|  | 100.00 | 16.2 |

In Example #4, granulated xylitol was crushed into a fine powder using a mortar and pestle. Lecithin and flavor powder were added, and the mixture was sifted to add airiness to the mixture. In this combination the flavor of the sexual enhancement lubrication powder was desirable and the sweetness thereof was acceptable. However, with sweetener/sialogogue (xylitol) added near the lower acceptable limit, when human saliva was added, the resulting flavor was undesirable, based on the combination of too little xylitol and lecithin. This example serves to illustrate the range of sweetener (such as xylitol) that may be added to achieve desirable sweetness and the effect the amount of sweetener has on the viscosity of the sexual lubricant based on the sweetener's interaction with the thickening agent.

Example #5

|  | % by weight | amount in grams |
| --- | --- | --- |
| Xylitol | 59.70 | 12 |
| Lecithin | .50 | 0.1 |
| Flavor powder (from Nature's flavors ™) | 39.80 | 8 |
|  | 100.00 | 20.1 |

In Example #5, granulated xylitol was crushed into a fine powder using a mortar and pestle. Lecithin and flavor powder were added, and the mixture was sifted to add airiness to the mixture. In this combination the sweetness and flavor of the sexual enhancement lubrication powder was desirable. However, with lecithin added near the lower acceptable limit, when human saliva was added, the viscosity of the sexual lubricant was too low to be a desirable sexual lubricant. This example serves to illustrate the range of thickening agent (such as lecithin) that may be added to achieve desirable sexual lubricant viscosity.

Example #6

|  | % by weight | amount in grams |
| --- | --- | --- |
| Xylitol | 58.82 | 12 |
| Lecithin | 1.96 | 0.4 |
| Flavor powder (from Nature's flavors ™) | 39.22 | 8 |
|  | 100.00 | 20.1 |

In Example #6, granulated xylitol was crushed into a fine powder using a mortar and pestle. Lecithin and flavor powder were added, and the mixture was sifted to add airiness to the mixture. In this combination the sweetness and flavor of the sexual enhancement lubrication powder was desirable. However, with lecithin added near the upper acceptable limit, when human saliva was added, the viscosity of the sexual lubricant was too high to be a desirable sexual lubricant. This example serves to further illustrate the range of thickening agent (such as lecithin) that may be added to achieve desirable sexual lubricant viscosity.

An edible sexual enhancement lubricant powder that is too sweet results in undesirable taste and can inhibit a sexual experience. Similarly, if lubricant that results from the combination of the dry sexual enhancement lubricant powder and saliva is too runny (i.e. low viscosity), the lubricant does not have the characteristic of being able to stay in place to provide adequate lubrication, and a less viscous lubricant does not reduce friction between body parts to a desirable level. Some friction is required in order to stimulate the sexual experience, so too little friction is undesirable, but too much friction can cause pain when body parts roughly slide along each other, so too much friction is also undesirable. If the lubricant is too thick, it will not coat the surfaces which are in contact each other sufficiently, resulting in incomplete lubrication. Also, if the lubricant is too thick (i.e. high viscosity), it may not reduce friction, also resulting in an undesirable experience. Additionally, sexual participants may find that a lubrication that is overly mucilaginous, viscid, gelatinous, glutinous, gooey, syrupy, thick, viscose, or slimy may be unappealing for sexual intimacy. Hence, embodiments of the edible sexual enhancement body lubrication powder, as described herein, may be provided in a composition that, when combined with saliva, obtains a viscosity that is similar to the viscosity of other common gel-like sexual lubricants.

While this invention has been described in conjunction with the specific embodiments outlined above, it is evident that many alternatives, modifications and variations will be apparent to those skilled in the art. Accordingly, the embodiments of the invention as set forth above are intended to be illustrative, not limiting. Various changes may be made without departing from the spirit and scope of the invention as defined in the following claims.

What is claimed is:

1. A dry, edible, sexual enhancement lubricant powder composition comprising:
   a dry, powdered sweetening agent which is also a sialogogue,
   a dry, powdered thickening agent, which is combined with the sweetening agent/sialogogue;
   a dry, powdered flavoring agent, which is combined with the sweetening agent/sialogogue and thickening agent
   the composition such that whereupon the addition of human saliva to the dry, powdered, edible composition, effectuates the transformation of the composition into a gel-like lubricant useable for sexual enhancement.

2. The composition of claim 1, wherein the flavoring agent comprises a dextrose base powder, and at least one natural flavor.

3. The composition of claim 1 wherein the dry, powdered sweetening agent which is also a sialogogue is xylitol, present in an amount from 43%-73% by weight of the total dry, edible, sexual enhancement lubricant powder composition.

4. The composition of claim 1 wherein the dry, powdered thickening agent is lecithin, present in an amount from 0.3%-3% by weight of the total dry, edible, sexual enhancement lubricant powder composition.

5. The composition of claim 1 wherein the dry, powdered flavoring agent is a dextrose base powder with at least one added natural flavor, the flavoring agent present in an amount from 26%-55% by weight of the total dry, edible, sexual enhancement lubricant powder composition.

6. The composition of claim 1 further comprising a coloring agent.

7. The composition of claim 1 further comprising a glow-in-the dark agent.

8. The composition of claim 1 further comprising a preserving agent.

9. A dry, edible, sexual enhancement lubricant powder composition comprising:
   dry, powdered xylitol, used as a sweetener/sialogogue;
   a dry, powdered gelatinizing viscosity enhancer which provides for an increase in the internal resistance of the composition when a liquid phase is added without substantially modifying other properties of the composition, improves suspension of dry powdered ingredients of the composition in a liquid phase, the gelatinizing viscosity enhancer being combined with the xylitol;
   a dry, powdered flavoring agent, which is combined with the xylitol and gelatinizing viscosity enhancer wherein the flavoring further comprises:
   a dextrose base powder, and
   at least one natural flavor;
   the composition such that whereupon the addition of human saliva to the dry, powdered, edible composition, effectuates the transformation of the composition into a viscous semi-rigid colloidal suspension useable as a personal lubricant.

10. The composition of claim 9 wherein the xylitol is present in an amount from 54%-66% by weight of the total dry, edible, sexual enhancement lubricant powder composition.

11. The composition of claim 9 wherein the xylitol is a finely ground powder.

12. The composition of claim 9 wherein the gelatinizing viscosity enhancer is lecithin and is present in the amount of from 0.9%-1.1% by weight of the total dry, edible, sexual enhancement lubricant powder composition.

13. The composition of claim 9 wherein the flavoring agent is present in an amount from 32%-45% by weight of the total dry, edible, sexual enhancement lubricant powder composition.

14. A:
   dry, edible, sexual enhancement lubricant powder composition created by a method comprising the steps of:
      crushing a sweetening agent which is also a sialogogue into a dry powder;
      rushing a thickening agent into a dry powder
      crushing a flavoring agent into a dry powder
      combining the crushed sweetening agent which is also a sialogogue, the crushed thickening agent, and the crushed flavoring agent to create a mixture; and
      sifting the mixture to add airiness;
      wherein the addition of human saliva to the mixture effectuates a transformations of the mixture into a gel-like lubricant useable for sexual enhancement.

15. The composition of claim 14 further comprising adding to the mixture a coloring agent.

16. The composition of claim 14 further comprising adding to the mixture a glow-in-the-dark agent.

17. The composition of claim 14 further comprising adding to the mixture a preserving agent.

18. The composition of claim 14 wherein the method further comprises grinding by mechanical force the components prior to mixing to ensure the components and the resulting composition are finely ground powders.

19. The composition of claim 14 wherein the step of sifting the mixture is performed at least once to add air to the composition in order to lower composition density and increase composition volume, resulting in a lighter, fluffier composition.

* * * * *